United States Patent [19]

Weiner et al.

[11] Patent Number: 5,626,873
[45] Date of Patent: May 6, 1997

[54] EMULSIONS

[75] Inventors: Alan L. Weiner, Lawrenceville, N.J.; Sharon Carpenter-Green, Gaffney, S.C.

[73] Assignee: The Liposome Company, Inc., Princeton, N.J.

[21] Appl. No.: 442,080

[22] Filed: May 16, 1995

Related U.S. Application Data

[60] Continuation of Ser. No. 927,114, Aug. 7, 1992, abandoned, which is a division of Ser. No. 318,774, Mar. 3, 1989, Pat. No. 5,171,737.

[51] Int. Cl.$^6$ .............................. A61K 9/66; A61K 38/00
[52] U.S. Cl. .............................. 424/455; 424/450; 514/2; 514/3; 252/302; 252/308
[58] Field of Search ........................... 514/2, 3; 424/450, 424/455; 252/302, 308

[56] References Cited

U.S. PATENT DOCUMENTS

| | | | |
|---|---|---|---|
| 3,934,013 | 1/1976 | Paulsen | 424/239 |
| 3,992,520 | 11/1976 | Gwatkin | 424/85 |
| 3,993,073 | 11/1976 | Zaffaroni | 128/260 |
| 4,474,912 | 10/1984 | Ozmeral | 523/337 |
| 4,533,666 | 8/1985 | Matsumoto | 514/277 |
| 4,720,353 | 1/1988 | Bell | 252/309 |
| 4,897,355 | 1/1990 | Eppstein | 435/240.2 |
| 5,171,737 | 12/1992 | Weiner | 514/3 |
| 5,204,112 | 4/1993 | Hope | 124/450 |

OTHER PUBLICATIONS

Trouet, *Recent Results Cancer Res* 75, 229–35, 1980.
Collins, *Cancer Research* 47, 735–39, 1987.
Griffin, et al., "Further Studies on Emulsion Systems", American Perfumer and Cosmetics, 81(9)1–8 (1966).
Madden, et al., "Stabilizaiton of Bilayer Structure for Unsaturated Phosphatidylethanolamines by Detergents", Biochemica et Biophysica Act, 684 (1982), 149–153.
Shinoda, et al., *Emulsions and Solubilzation*, 1986, John Wiley & Son, Inc. pp. 1–9, 55–93.
Tyle, "Liquid Crystals and Their Applications in Drug Delivery", from *Controlled Release of Drugs: Polymers and Aggregate Systems*, Morton Rosoff, ed, VCH Publishers(1989), pp. 125–162.
Weiner, "Lamellar Systems for Drug Solubilization", from *Liposomes, From Biophysics to therapeutics*, Ostro, ed., Marcel Dekker, Inc., New York, 1987.

*Primary Examiner*—Cecilia J. Tsang
*Assistant Examiner*—David Lukton
*Attorney, Agent, or Firm*—Kenneth B. Rubin

[57] ABSTRACT

A novel oil and water emulsion useful for delivery of a bioactive agent is disclosed. The emulsion comprises a first HLB requirement amount of surfactant dioleoyl phosphatidylethanolamine. In particular embodiments the emulsion includes a secondary surfactant other than dioleoyl phosphatidylethanolamine except in the limiting case wherein the HLB requirement is the HLB value of dioleoyl phosphatidylethanolemine in which case the the HLB requirement amount of a secondary surfactant is 0. By appropriate selection of dioleoyl phosphatidylethanolamine to secondary surfactant ratios, it is possible to prepare emulsions for pharmaceutical delivery of a bioactive agent using an oil phase having a required HLB value up to about 17.4. Above a required HLB value of about 17.4, dioleoyl phosphatidylethanolamine may be used to reduce the amount of secondary surfactant required to form an emulsion.

12 Claims, 6 Drawing Sheets

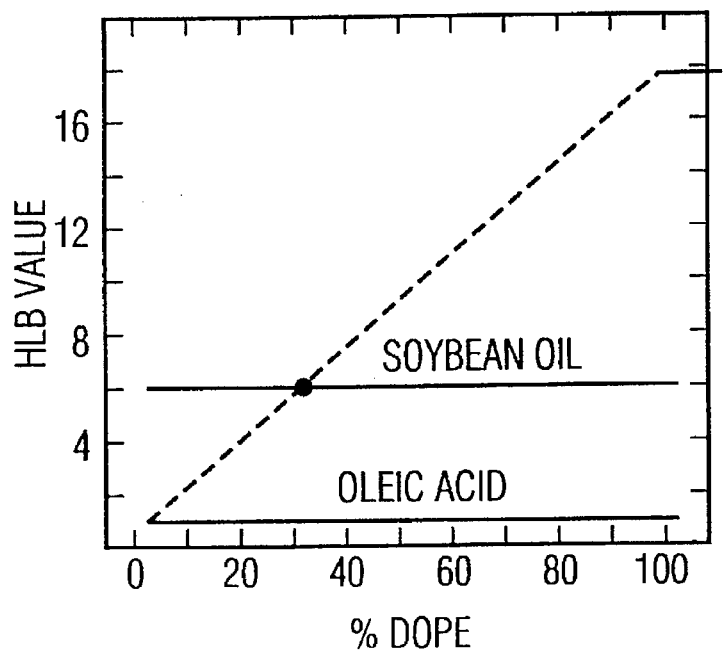
FIG. 1A
FIG. 1B
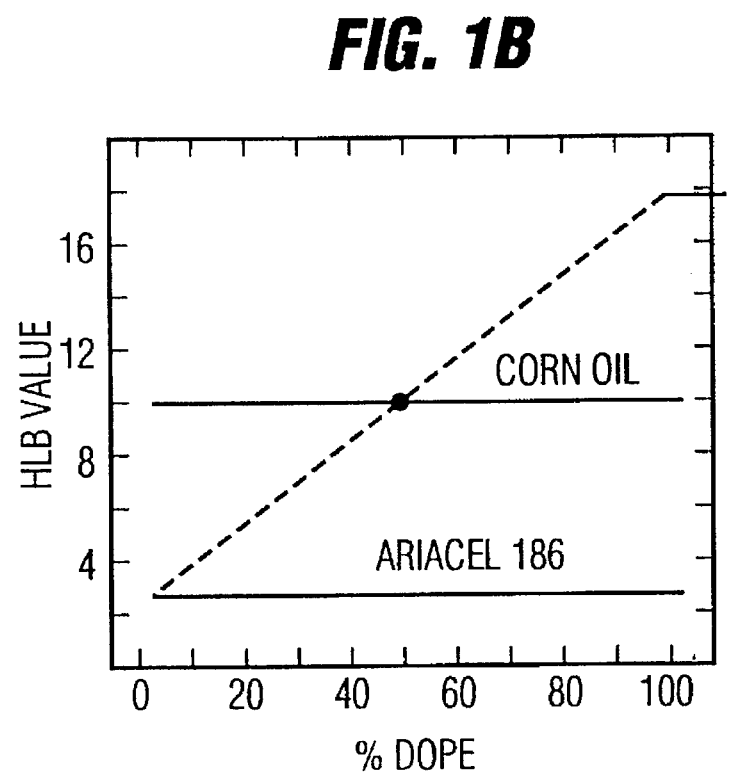

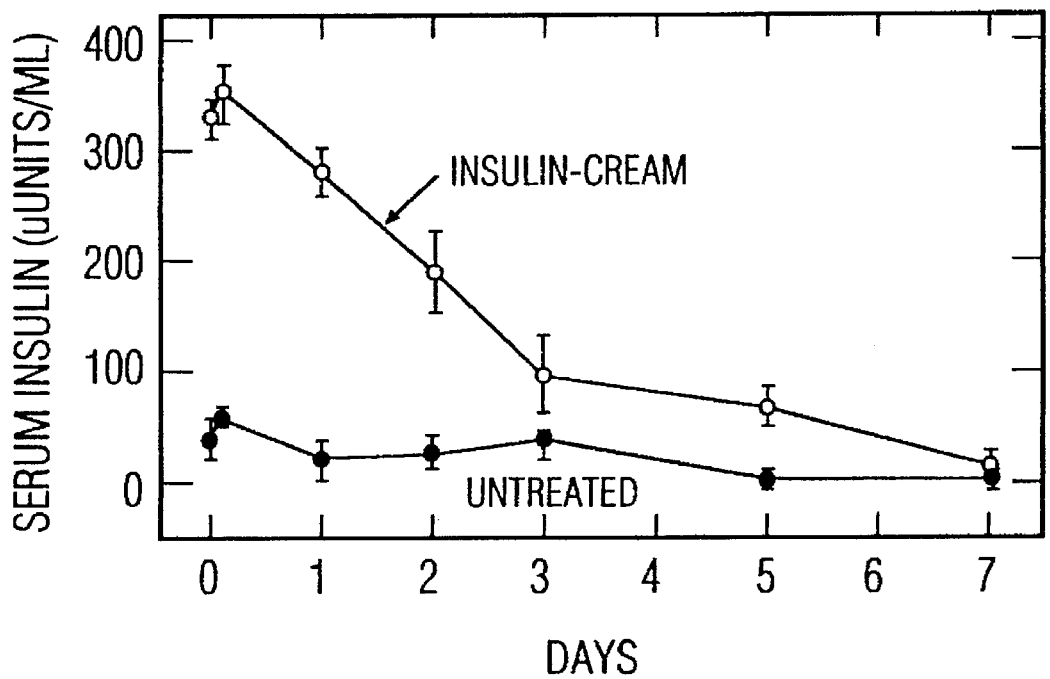
FIG. 6A
FIG. 6B
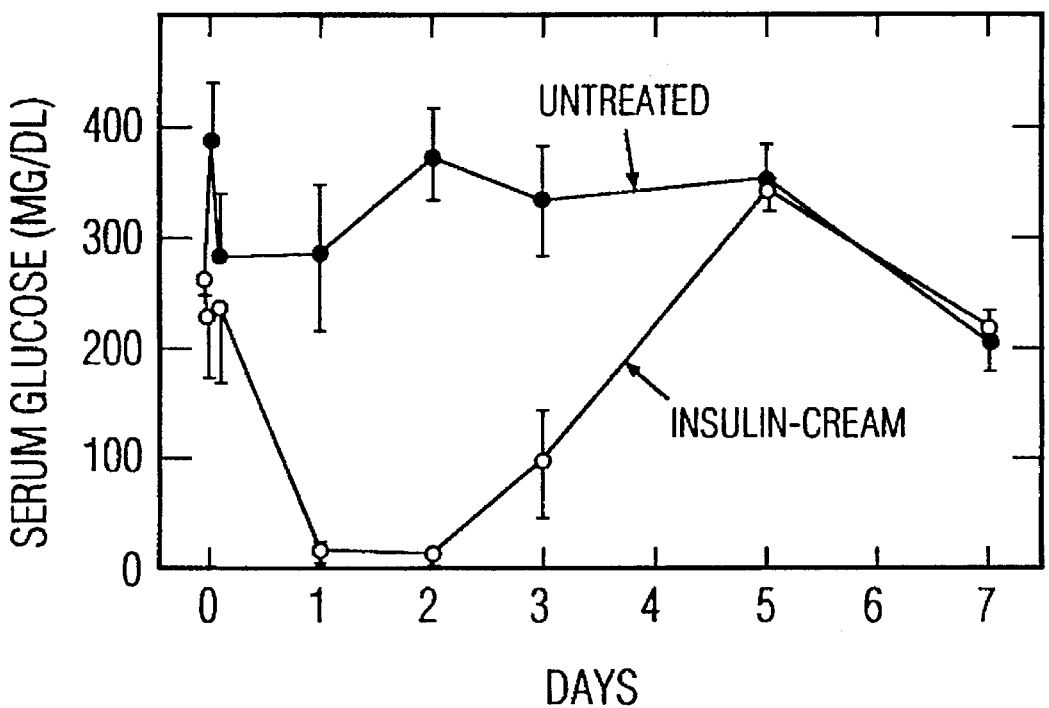

EMULSIONS

This application is a continuation of U.S. Ser. No. 07/927,114, filed Aug. 7, 1992 and now abandoned, which is a division of U.S. Ser. No. 07/318,774, filed Mar. 3, 1989 and now U.S. Pat. No. 5,171,737.

BACKGROUND OF THE INVENTION

The present invention relates to emulsions for bioactive agent delivery and, more particularly, to emulsions prepared from phospholipids having high HLB values and preferably of low toxicity as well as homogenous and stable.

It has been proposed to deliver a bioactive agent (e.g. a drug, imaging agent or diagnostic agent), especially parenterally, to a patient by formulating such bioactive agent in an emulsion. Thus, typically, the bioactive agent is combined with an oil phase, a water phase and a surfactant. One problem with such delivery systems, however, has been the limited availability of surfactants which are considered biocompatible or non-toxic. It is well known that certain surfactants induce hemolysis while others have been shown to possess toxic effects relative to protein denaturation, capillary permeability, membrane bound enzyme activity and cellular histamine release.

In view of the above-described toxicity problems, naturally derived surfactants such as phospholipids have been proposed for formulating parenteral bioactive agent emulsions. For example, phosphatide stabilized emulsions of soy, safflower and cottonseed oil are currently accepted for administration to humans as intravenous nutrition supplements. Phosphatide emulsion systems have also been applied to the delivery of prostaglandin E1, corticosteroids, and indomethacin.

The bulk surfactant employed in the preparation of phospholipid emulsions is lecithin or phosphatidylcholine, it being understood that lecithin typically includes mixtures of various phosphatides. For example, commercial lecithin as supplied for intravenous fat emulsions is made up predominantly of phosphatidylcholine and phosphatidylethanolamine, with minor percentages of lysophosphatidylcholine, sphingomyelin, phosphatidic acid, phosphatidyl inositol, phosphatidylserine, and cholesterol.

While the phosphatide surfactants described above overcome the toxicity problems associated with the use of most conventional surfactants in parenteral emulsions, they have been somewhat limited in their application due to their narrow hydrophile-lipophile-balance (HLB) range. As is known by persons skilled in the art, the empirically determined HLB value of a surfactant designates the ability of such surfactant to emulsify oils having HLB requirements between about 1 and 20 but further including materials such as perfluorocarbons. Currently known emulsion systems based on phosphatide surfactants are based on the ability of the surfactants to emulsify oils having a relatively narrow HLB requirement of about 6. Thus, for example, phosphatidylcholine which is the primary ingredient in phosphatide mixtures has a required HLB value of only 7.6 when tested in its pure state. Therefore, oils such as corn oil, castor oil, mineral oil and palm oil having higher HLB requirements, e.g., above 8, could not be stabilized with conventional phosphatide surfactants.

Not surprisingly, therefore, emulsions for parenteral bioactive agent delivery have gained only a very limited acceptance. Thus, while a wide variety of commercial surfactants having HLB values ranging from 1–20 are available, precious few of those surfactants are suitable for parenteral administration to a patient. Additionally, the few surfactants suitable for parenteral administration can form stabilized emulsions with an oil only at a very narrow HLB range, which is far too low for emulsification of many oils.

SUMMARY AND OBJECTS OF THE INVENTION

In view of the foregoing limitations and shortcomings of prior art emulsions for parenteral bioactive agent delivery as well as other disadvantages known to those in the art, it should be apparent that there still exists a need in the art for a parenteral emulsion which is non-toxic and which includes an oil phase having a wide range of HLB values. It is, therefore, a primary objective of the present invention to fulfill that need by providing a phosphatide which is non-toxic and which, unexpectedly, has an HLB at the upper range of the scale which can be used alone or mixed with other phosphatides to prepare emulsions from oils having a wide range of required HLB values.

It is a further object of the present invention to provide non-toxic, parenteral emulsions in the form of gels or creams into which a bioactive agent is readily incorporated.

Yet another object of the present invention is to provide a non-toxic parenteral emulsion which is stable.

In one embodiment this invention comprises a water and oil emulsion comprising a first HLB requirement amount of primary surfactant dioleoyl phosphatidyhthanolamine. In particular embodiments the oil is a pharmaceutically acceptable oil such as corn oil, castor oil or mineral oil. In a further embodiment the emulsion further comprises a second HLB requirement amount of a secondary surfactant such as phosphatidylcholine. In yet further embodiments of the invention the emulsion is characterized in that the secondary surfactant has an HLB value such that the first and second HLB requirement amounts of primary and secondary surfactants result in an HLB value equal to the HLB requirement of said oil. Particular examples of this invention entail water and oil emulsions wherein the oil has an HLB requirement between about 17.4 and about 20 or between about 8 and about 17.4 or about 10 and 17.4 as well as wherein the secondary surfactant is phosphatidylcholine.

In additional embodiments the emulsions of this invention are according to the formula:

$$P \times (HLB_1) + 1 - P \times (HLB_2) = HLB_3$$

wherein:

P represents the percentage by weight of dioleoyl phosphatidylethanolamine being the first HLB requirement amount;

1-P represents the percentage by weight of secondary surfactant being the second HLB requirement amount;

$HLB_1$ represents the HLB value of dioleoyl phosphatidylethanolamine;

$HLB_2$ represents the HLB value of the secondary surfactant; and, $HLB_3$ represents the HLB requirement of the oil.

In some embodiments emulsions of this invention are understood to include a bioactive agent and further wherein said bioactive agent includes a hydrophobic moiety. Particular bioactive agents are perfluorocarbon, protein, adjuvant, immunogen or insulin.

Various emulsions of this invention are in the form of a cream or gel.

This invention additionally includes a method of preparing a water and oil emulsion (which may include a bioactive agent) comprising combining with the water and oil a first HLB requirement amount of surfactant dioleoyl phosphatidylethanolamine. In some embodiments of the method the emulsion further comprises additionally combining with the water and oil a second HLB requirement amount of a secondary surfactant such as phosphatidylcholine. In further embodiments of preparing the emulsion the first HLB requirement amount of dioleoyl phosphatidylethanolamine and second HLB requirement amount of secondary surfactant results in an HLB value equal to the HLB requirement of said oil. Particular examples of this invention entail the method of preparing the emulsion of water and oil emulsions wherein the oil has an HLB requirement between about 17.4 and about 20 or between about 8 and about 17.4 or about 10 and 17.4 as well as wherein the secondary surfactant is phosphatidylcholine.

Included is the method of preparing the emulsion according to the formula:

$$P \times (HLB_1) + 1 - P \times (HLB_2) = HLB_3$$

wherein:

P represents the percentage by weight of dioleoyl phosphatidylethanolamine being the first HLB requirement amount;

1-P represents the percentage by weight of secondary surfactant being the second HLB requirement amount;

$HLB_1$ represents the HLB value of dioleoyl phosphatidylethanolamine;

$HLB_2$ represents the HLB value of the secondary surfactant; and, $HLB_3$ represents the HLB requirement of the oil.

In a further embodiment this invention includes a method of treating an animal, including a human, in need of such treatment comprising the step of administering (such as subcutaneously or intramuscularly) to the animal a therapeutically effective amount of a water and oil emulsion including a bioactive agent and comprising a first HLB requirement amount of surfactant dioleoyl phosphatidylethanolamine. In some embodiments the emulsion of the method may further include a second HLB requirement amount of a secondary surfactant such as phosphatidylcholine. In emulsions of the method the bioactive agent may be a perfluorocarbon, protein, adjuvant or immunogen as well as an insulin.

BRIEF DESCRIPTION OF THE DRAWINGS

FIGS. 1A–1B are graphs of the calculated HLB value of DOPE in a soybean oil/oleic acid system or a corn oil/Arlacel 186™ system;

FIGS. 6A–6B are graphs of the in vivo diffusion of insulin to the blood stream of diabetic rats from emulsions administered s.c. with subsequent depression of serum glucose values as a function of time.

DETAILED DESCRIPTION OF THE INVENTION

The components employed to formulate the water and oil emulsions of the present invention are (1) the dioleoyl phosphatidylethanolamine (which is understood to be in the 18:1 c/18:1 c configuration), (2) an HLB requirement amount of secondary surfactant (which includes phosphatides). In some instances multiple secondary surfactants may be used. These secondary surfactants may have an HLB higher or lower than the dioleoyl phosphatidylethanolamine. Of particular note is the condition wherein the HLB requirement of secondary surfactant is 0 and thus no secondary phosphatide or surfactant is required. A bioactive agent may be incorporated into the emulsion, which may be in the form of a gel or cream, and the emulsion then administered in a number of ways such as parenterally to a patient.

18:1 c/18:1 c dioleoyl phosphatidylethanolamine (DOPE) denotes a phosphatide having two 18-carbon chains with one cis- double bond in each chain. DOPE is commercially available, for example, from Avanti Polar Lipids, Birmingham, Ala.

Emulsions of this invention are termed stable if no visible phase separation occurs after 24 hours standing at about 15°–20° C. More preferably the stable emulsions show no visible phase separation after one week and most preferably after one month. Emulsions are termed homogenous if there is no visible oil phase or water phase.

Emulsions of this invention are preferably of low toxicity. Low toxicity emulsions shall be understood to mean non-necrosing of adjacent tissue in a treated subject (exclusive of necrosis caused by the bioactive agent if present).

The HLB value of DOPE was determined to be approximately 17.4. The results of these tests are shown in FIG. 1. To determine the HLB value, a one gram test system was set up and a final 5% surfactant concentration utilized. DOPE was eliquoted from a solution in chloroform and each aliquot was blown to dryness in a 12×75 mm glass tube under a stream of nitrogen. To the dry phospholipid film was added an aliquot of either oleic acid or Arlacel 186™ (mono and diglycerides of fat forming fatty acids)(ICI Americas, Inc., Wilmington, Del.). The surfactant mixture was brought to 0.5 grams with either soybean or corn oil. Surfactants were then blended into the oil phase with a small stir rod attached to a high speed motor. Occasional sonication assisted in achieving a homogeneous blend.

A 0.5 gram aliquot of water was added to the oil/surfactant blend and the total mixture was capped, subject to vortexing for 1 minute, and then allowed to stand undisturbed. Observations on phase separations were typically recorded over a 1–2 week period.

The DOPE HLB value of about 17.4 puts it within the same range as the non-ionic surfactant Polysorbate 20™ (polyoxyethylene (20) sorbitan monolaurate)(ICI Americas, Inc., Wilmington, Del.).

Figure 2:
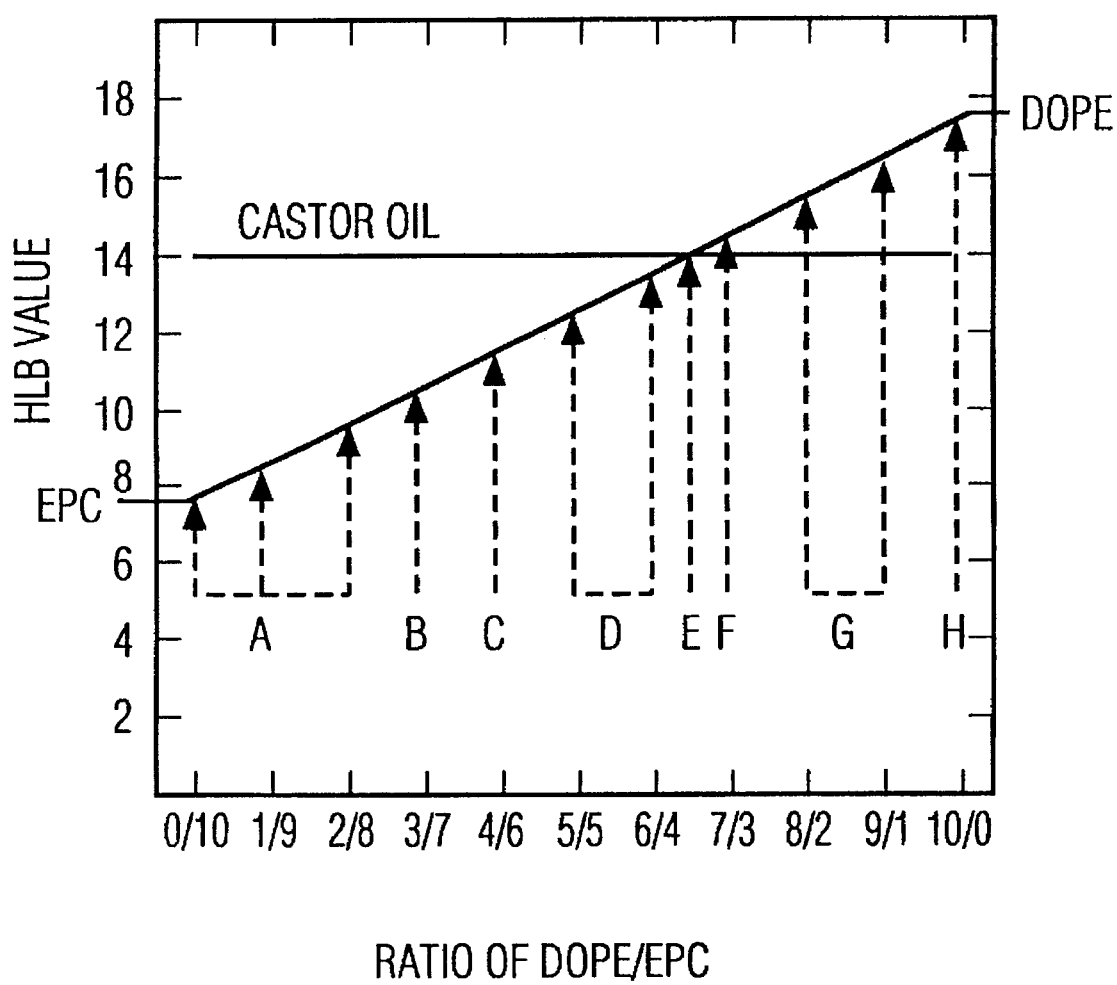
FIG. 2 is graph of the HLB value of a mixture of DOPE and EPC in a castor oil emulsion as a function of the ratio DOPE/EPC.

Supplementations of DOPE with other surfactants allows for the formation of emulsions with oils which have varying HLB requirements. More specifically, by combining DOPE (17.4 HLB) with other phosphatides (which are surfactants) having lower HLB values, emulsification of oils having HLB requirements up to about 17.4 are possible. For example, any oil possessing an HLB requirement between about 7.6 and about 17.4 is capable of producing a stable emulsion with water at the specified ratio of DOPE to EPC that matches its HLB number. To this end, castor oil was deliberately selected as a test ingredient since this oil has an unusually high HLB requirement of 14. Therefore, the theoretically predicted ratio of DOPE to EPO which results in and HLB value of 14 is 65/35 respectively, obtained by solving for the equation (P)(17.4)+(1-P)(7.6)=14 where P represents the percentage by weight of dioleoyl phosphatidylethanolamine end 1-P represents the percentage by weight of secondary surfactant, here EPC. The actual experimental results are depicted in FIG. 2. As predicted, it was observed that at precisely the ratio of 65/35 (DOPE/EPC) (Arrow E), a maximally homogeneous emulsion is produced. Unexpectedly, it is also observed that at this ratio immediate gelation of the emulsion occurred. Emulsion in the gelled state is a preferred stable form of emulsion. At slight deviations from this ratio, such as 60/40 (Arrow D) or 70/30 (Arrow F), gelation was noticeable only after a 1 to 2 week period offering sufficient stability for many applications. Further deviation from these ratios (Arrows A–C, G, H) eliminated the gelation effect entirely. At HLB requirements above about 17.4 a secondary surfactant (which will likely be a detergent characterized by high toxicity) is required to form a stable emulsion. However less of such secondary surfactant is required when admixed with DOPE than when mixed with, for example, phosphatidylcholine. The use of less detergent in an emulsion results in lessened toxicity.

Figure 3:
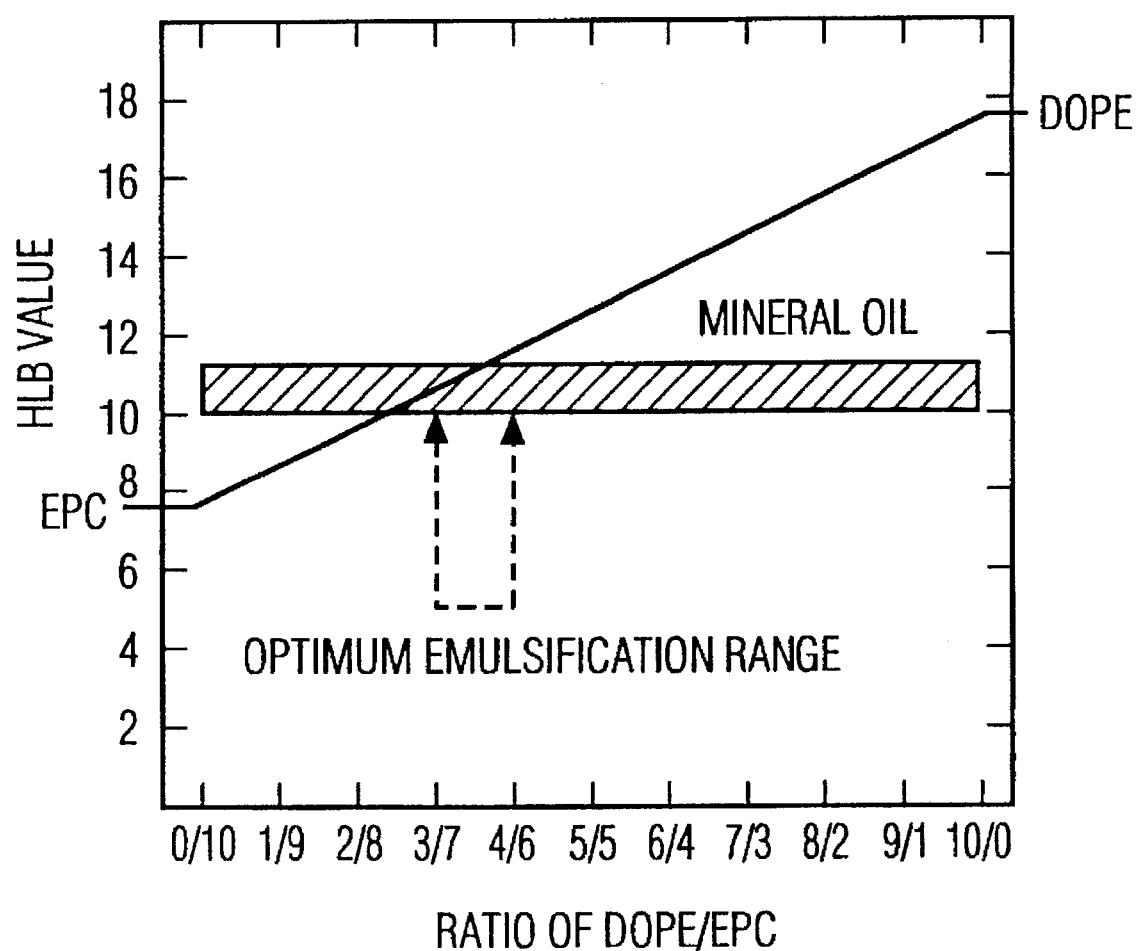
FIG. 3 is a graph of the HLB value of a mixture of DOPE and EPC in a mineral oil emulsion as a function of the ratio DOPE/EPC.

It is apparent that the potential of producing other gelled emulsions with this surfactant combination hinge on emulsification of oils or hydrophobic materials which display fairly high initial viscosities. As an example, castor oil has an inherent viscosity of 293.4 centistokes at 100° F. Another test material having a higher viscosity is mineral oil. FIG. 3 illustrates that emulsification of mineral oil at its required HLB value of 10–11, with a 35/65 ratio of DOPE to EPC, results again in a gel-like state.

The secondary surfactant, if a phosphatide, can be selected from virtually any of the various known phosphatides. In pharmaceutical application the phosphatide is preferably compatible with the bioactive agent being employed as well as capable of parenteral administration. Particularly preferred is egg phosphatidylcholine (EPC) which is available commercially, for example, from Avanti Polar Lipids. Other phosphatides which can be employed in combination with DOPE include phosphatidyl glycerol, phosphatidyl inositol, phosphatidyl serine, phosphatidic acid, sphingomyelin, and cardiolipin. When combined with DOPE, EPC enables preparation of emulsions from oils having HLB requirements ranging from about 7.6 to about 17.4. Above about 17.4 a different secondary surfactant is required such as ethoxylated nonylphenols or ethoxylated alkylphenols.

In general use any oil may be employed with this invention. In pharmaceutical use for the oil phase there may be employed any oil which is compatible with parenteral administration and does not otherwise adversely affect the bioactive agent. It is noted that selection of viscous oils, such as mineral oil or castor oil, enables formulation of gels or creams. It is found that the consistency of gelled emulsions could be regulated by increasing the total surfactant concentration above the 5% level (w/w) which was used in initial test trials. At 20% surfactant levels, a cream or "mousse"-like texture was achieved. These creams were resistant to phase separation upon addition to water or buffer and flowed readily without separation through syringe needles. Additionally, bioactive agents are readily incorporated into such creams.

The HLB value of an oil will, of course, determine the HLB requirement of the DOPE/surfactant employed. "HLB requirement" and "HLB requirement amount" are terms advisedly and specifically used herein. Where the HLB value of the oil is about 17.4 the HLB requirement amount for DOPE ("first HLB requirement") is P and for the secondary surfactant ("second HLB requirement") is 0 and secondary surfactant is not required to form a stable emulsion. In all other cases the second HLB requirement of secondary surfactant will be 1-P in the formula:

$$P \times (HLB_1) + 1 - P \times (HLB_2) = HLB_3$$

wherein:

P represents the percentage by weight of dioleoyl phosphatidylethanolamine being the first HLB requirement amount;

1-P represents the percentage by weight of secondary surfactant being the second HLB requirement amount;

$HLB_1$ represents the HLB value of dioleoyl phosphatidylethanolamine;

$HLB_2$ represents the HLB value of the secondary surfactant; and, $HLB_3$ represents the HLB requirement of the oil.

The "first and second HLB requirement amount" is the weight of the primary (DOPE) or secondary surfactant (respectively) required in view of the MLB value of the oil.

Useful pharmaceutical oils in addition to mineral oil and castor oil discussed above include con oil, soybean oil, cottonseed oil, peanut oil, safflower oil, and palm oil.

Generally, any bioactive agent which is administered parenterally may be formulated into the emulsion of the present invention. Included among such bioactive agents are insulin, indomethacin, diazepam, miconazole, and amphotericin B. Bioactive agent to the present include but are not limited to antibacterial compounds such as gentamicin, antiviral compounds such as rifampacin, antifungal compounds such as amphotericin B, anti-parasitic compounds such as antimony derivatives, antineoplastic compounds such as vinblastine, vincristine, mitomycin C, doxorubicin, daunomycin, methotrextate, and cisplatin, among others, proteins such as albumin, toxins such as dipthetis toxin, enzymes such as catalase, hormones such as estrogens, neurotransmitters such as acetylcholine, lipoproteins such as alpha-lipoprotein, glycoproteins such as hyaluronic acid, immunoglobulins such as IEG, immunodulators such as the interferons or the interleukins, dyes such as Arsenazo III, radiolabels such as $^{14}C$ radio-opaque compounds such as $^{99}Te$, fluorescent compounds such as carboxy fluoroscein, polysaccharides such as glycogen, cell receptor binding molecules such as estrogen receptor protein, non-steroidal anti-inflammatories such as indomethacin, salicylic acid acetate, ibuprofen, sulindac, piroxicam, and naproxen; anti-inflammatories such as dexamethasone, antiglaucomic agents such as timolol or pilocarpine, anesthetics such as dibucaine, nucleic acids such as thymine, polynucleotides such as RNA polymers. Also included are various bioactive chemical entities such as peptides, hormones, toxins, enzymes, neurotransmitters, lipoproteins, glycoproteins, immunomodulators, immunoglobulins, polysaccharides, cell receptor binding molecules, nucleic acids, polynucleotides, and the like, as well as biological tracer substances such as dyes, radio-opaque agents, and fluorescent agents.

One embodiment of the present invention employs hydrophobic bioactive agents or, at the very least, agents having a hydrophobic portion. Such hydrophobic agents facilitates slow, long term bioactive agent delivery.

In a particular embodiment the emulsion is usefully employed with blood substitutes such as perfluorocarbons.

The HLB property of DOPE offers results superior to other lipids such as phosphatidylcholine in the emulsification of perflurocarbons as described in U.S. Pat. No. 4,423,077 to Sloviter the teachings of which are incorporated herein by reference. Perfluorocarbons are usually formulated into an emulsion by using surfactans like Pluronic F-68™ (block co-polymers of propylene and ethylene oxides, BASF Corp., Parsippany, N.J.), which has a reported HLB value of 29. However Plurontc F-68™ is highly toxic. EPC is less toxic but does not come as close to matching the high HLB requirement of the perfluorocarbons as does DOPE. Stable perfluorocarbon emulsion are used as blood substitutes and were prepared by blending first the water soluble ingredients together by sonication followed by gradual addition of the perfluorocarbon with continuous sonication. Conveniently perfluorocarbon comprises from about 30 to about 75% (w/v) of the final mixture and DOPE may comprise from about 5 to 20% (w/v). The various proportions are however, arrived at by recourse to the HLB values of the perfluorocarbons and the HLB requirements of DOPE and secondary surfactants.

Formulation of emulsions can be carried out in any fashion known to those skilled in the art. In one embodiment formulation comprises first combining DOPE or DOPE and secondary surfactant with oil phase to form an oil/surfactant phase. Such oil/surfactant phase is then blended with the bioactive agent. Finally, the aqueous phase is added to the blend to form a stable and homogeneous emulsion.

It is noted that the emulsions of the present invention can be formulated in accordance with the techniques described by P. K. Hansrani, S. S. Davis, and M. J. Groves (1983) "The Preparation and Properties of Sterile Intravenous Emulsions", J. Parent Sci. Tech., 37, 145–150 and M. Shinoda and S. Friberg, (1986) Emulsions and Solubilization, John Wiley and Sons, New York, pp 125–158 incorporated herein by reference.

To formulate emulsions of the present invention in the form of creams ratios of EPC and DOPE between 0 and 100% were prepared in 10% increments (w/w). Test systems with mineral oil or castor oil were formulated to determine the optimum surfactant blend which produced maximally stable and homogeneous emulsions. It was observed that at EPC:DOPE ratios which resulted HLB values at or near the required HLB of each of these oils (castor, 14; mineral, 10) a gel state developed. Conveniently using the specific surfactant ratio at the required HLB value of each oil (65:35 DOPE:EPO for castor oil; 35:65 DOPE:EPC for mineral oil), creams were produced by establishing the total phosphatide content at from about 10% to about 30% and preferably about 20%.

Formulation of insulin containing creams comprised blending insulin (in powder form) into the oil/surfactant phase prior to addition of the aqueous phase, conveniently at atmospheric pressure and about 15°–25° C. The resulting mixture was devoid of any bioactive agent crystals when blended completely.

The compositions of this invention with or without bioactive agents can be processed in accordance with conventional methods of galenic pharmacy to produce medicinal agents for administration to patients, e.g., mammals including humans or in other applications.

This invention can be employed as pharmaceutical compositions in admixture with conventional excipients, i.e., pharmaceutically acceptable organic or inorganic carrier substances suitable for parenteral, enteral (e.g., oral or inhalation) or topical application which do not deleteriously react with the active compositions or alter emulsion stability. Suitable pharmaceutically acceptable carriers include but are not limited to water, salt solutions, alcohols, gum arabic, benzyl alcohols, gelatine, carbohydrates such as lactose, amylose or starch, magnesium stearate, talc, silicic acid, hydroxy methylcellulose, polyvinyl pyrrolidone, etc. The pharmaceutical compositions can be sterilized and if desired mixed with auxiliary agents, e.g., lubricants, preservatives, stabilizers, wetting agents, salts for influencing osmotic pressure, buffers, coloring, flavoring and/or aromatic substances and the like which do not deleteriously react with the bioactive agents or emulsions of this invention. They can also be combined where desired with other bioactive agents, e.g., vitamins.

For parenteral application, particularly suitable are injectable, sterile, emulsions, or implants, including suppositories. Ampoules are convenient unit dosages of the pharmaceutical compositions.

For oral application of the emulsions and pharmaceutical compositions, particularly suitable are dragees, liquids, drops, suppositories, soft gels, or capsules. A syrup, elixir, or the like can be used wherein a sweetened vehicle is employed.

Sustained or directed release pharmaceutical compositions can be formulated, e.g., soft gels wherein the active component is protected with differentially degradable coatings, e.g., by microencapsulation, multiple coatings, etc.

For topical application, there are employed as nonsprayable forms, viscous to semi-solid or solid forms comprising a carrier compatible with topical application and having a dynamic viscosity preferably greater than water. Suitable formulations include but are not limited to emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon. Parenteral administration is preferred.

Generally, the compositions of this invention are dispensed in unit dosage form comprising a therapeutically effective amount of bioactive agent in a pharmaceutically acceptable carrier per unit dosage. They are also incorporated in topical formulations comprising a therapeutically effective amount of bioactive agent. Therapeutically effective shall mean sufficient bioactive agent to achieve the desires biological result.

It will be appreciated that the actual preferred amounts of bioactive agents in a specific case will vary according to the specific compositions being utilized, the particular compositions formulated, the mode of application, and the particular situs and organism being treated. Dosages for a given host can be determined using conventional considerations, e.g., by customary comparison of the differential activities of the subject compositions and of a known agent, e.g., by means of an appropriate, conventional pharmacological protocol.

Emulsions of the present invention are substantially less irritating than comparable formulations with surfactants replacing DOPE when injected locally. Incorporation of pertinacious substances is easily effected within such emulsions and sustained delivery over one week from subcutaneous inaction was demonstrated with insulin as a model compound (FIG. 6).

EXAMPLE 1

Formulation of Castor Oil/Insulin Cream

Preparation:

A castor oil cream was prepared consisting of 39.8% castor oil, 39.8% phosphate buffered saline, 13% DOPE, 7% EPC (as secondary surfactant), and 0.4% insulin (w/w). This corresponds to a 65:35 (w/w) DOPE:EPC ratio respectively (HLB value 14). The cream was prepared by blending all of the ingredients in a T-line laboratory (Talboys Engineering Corp., Emerson, N.J.) for 10–15 minutes. For in vitro release studies an aliquot of 14C-methyl insulin was added into the oil phase (0.2 uCi per gram of final cream).

Figure 5:
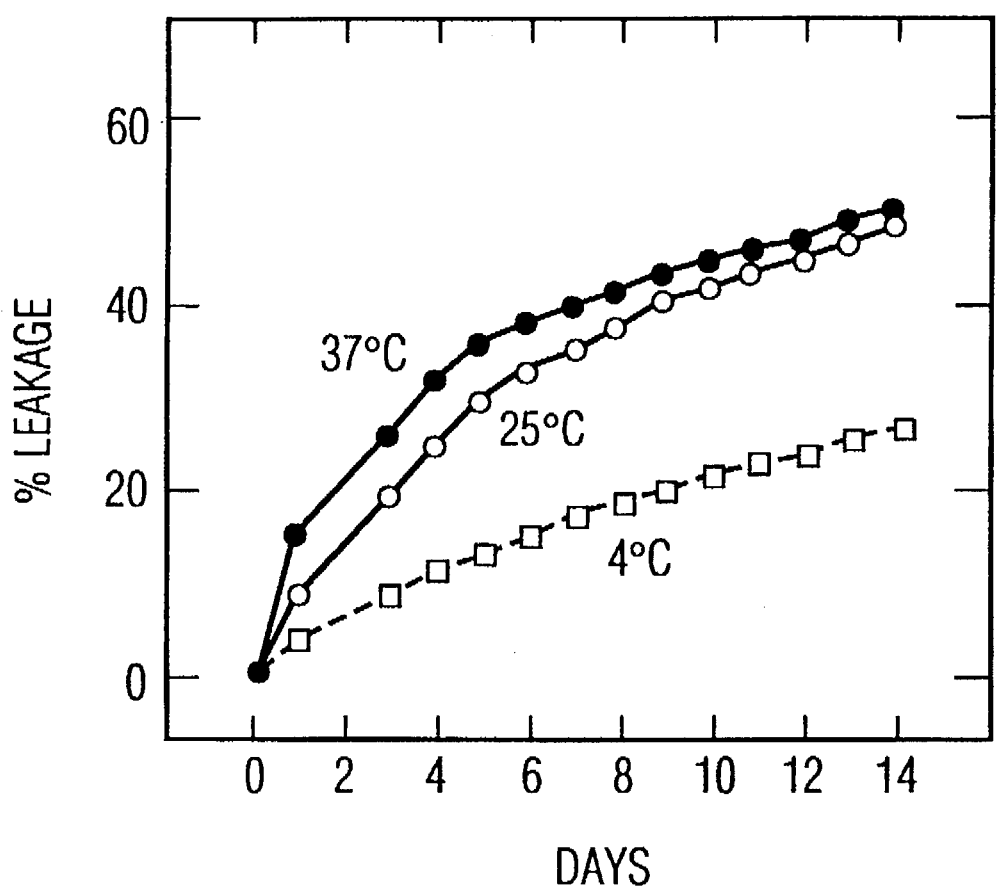
FIG. 5 is a graph the in vitro diffusion of insulin from an emulsion as a function of time.

Drug Release In Vitro:

Duplicate 1 ml samples of the castor oil cream were aliquoted into dialysis tubing (MW cutoff 50,000, Spectropor 7, Spectrum Medical Industries, Inc., Los Angeles, Calif.). A 1 ml sample of phosphate buffered saline ("PBS"), pH 7.4 was added into the bag which was then sealed and placed into 50 mls of the PBS. Bags were held in solution with stirring at 4° C., 25° C. and 37° C. over a two-week period. For the 4° C. and 25° C. samples the 50 ml of PBS was replaced with 50 ml of fresh PBS every 4 days. In the 37° C. sample the PBS was replaced every day. Diffusion of the 14C-insulin marker was monitored by counting a 1 ml aliquot of the dialysate each day. The withdrawn 1 ml sample was replaced with a fresh 1 ml aliquot of PBS. The results are shown in FIG. 5 Incubation at an elevated temperature, and with daily replacement of the incubation PBS, release of insulin proceeds gradually from the cream over a two-week period (FIG. 5). The release rate decreases within this time period, with 40–50% of the total insulin having diffused. At lower temperatures, the release of bioactive agent proceeds even more gradually and appears to be linear within this timeframe.

Drug Release In Vivo:

Diabetes in rats was developed by streptozotocin injection as described in Weiner, et al., "Liposome-collagen Gel Matrix: a Novel Sustained Drug Delivery System", *J. Pharm. Sci.*, 74:922–925 (1985), incorporated herein by reference. Assessment of diabetes was facilitated by monitoring water consumption, urine volume, serum insulin levels, and serum and urine glucose concentrations. Treated rats received a 1.0 ml subcutaneous injection of castor oil cream split containing insulin in two 0.5 ml injections in each leg. At various times after injection a 100 ul blood sample was collected by retro-orbital sampling. Serum was assayed for insulin concentration by radio-immunoassay and for glucose concentration by colorimetric/enzymatic coupled assay (Sigma Kit 510).

The release of insulin from castor oil cream in vivo is demonstrated in FIG. 6. High serum levels of insulin were observed within 3 hours of the S.C. injection. Although a slight depression of serum glucose was evident within 3–6 hours, the maximum changes were noted within a 24-hour period. A slow linear decay of serum insulin levels was observed over a one-week interval.

EXAMPLE 2

Formulation of Castor Oil/Sucrose Cream

Sucrose-containing creams ("sucrose creams") were formulated in a similar manner to the creams of Example 1, except that the sucrose was blended into the aqueous phase. A sucrose cream was prepared comprising 37.5% castor oil, 37.5% water, 13% DOPE, 7% EPC (secondary surfactant), and 5% sucrose (w/w). Sucrose cream was prepared by blending all of the ingredients in a laboratory for 10–15 minutes. The resulting mixture was devoid of any bioactive agent crystals when blended completely. A 0.45 uCi aliquot of 14C-sucrose was added to the aqueous phase per gram of final sucrose cream.

Figure 4:
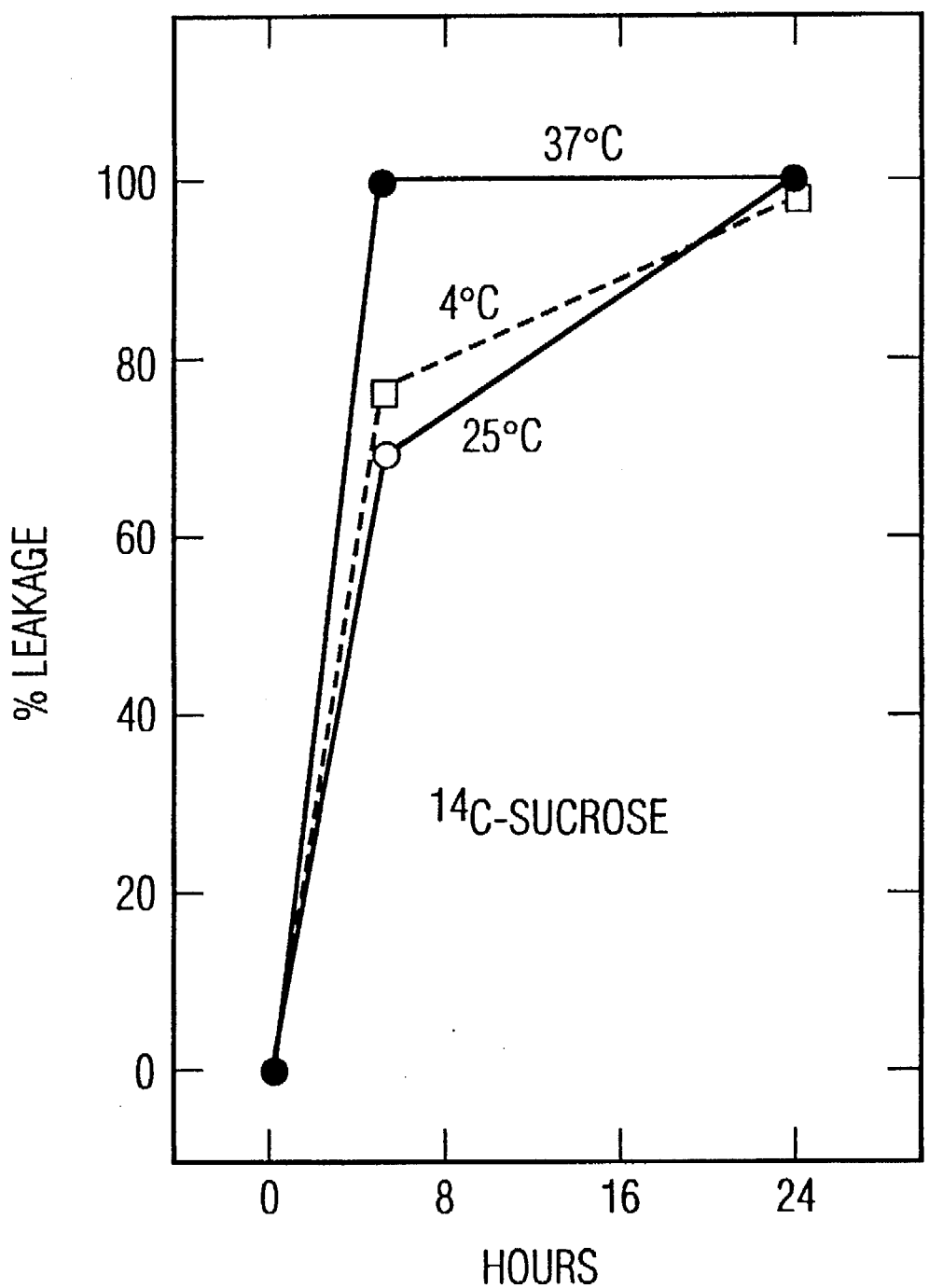
FIG. 4 is a graph of the in vitro diffusion of sucrose from an emulsion as a function of time.

Drug Release In Vitro:

Leakage of sucrose from sucrose cream was monitored over a 24-hour period without replacement of buffer. Samples of sucrose cream (0.1 ml) were aliquoted into 12×75 mm tubes to which was added 1 ml of PBS. Tubes were capped and held at 4° C., 25° C. and 37° C. At 5 and 24 hours a 0.1 ml aliquot was removed from the PBS and analyzed for 14C-sucrose. As shown in FIG. 4, diffusion of an aqueous miscible sucrose proceeded rapidly, with almost complete release into PBS solution occurring within 6 hours.

EXAMPLE 3

Formulation of Perflurocarbon Emulsion

An emulsion comprising perfluorotripropylamine 20% (w/v); 0.6% DOPE, 0.7% pluronic F-68 (Green Cross, Japan); 3% hydroxymethyl starch; 0.8% glycerol; 0.6% sodium chloride; 0.034% potassium chloride; 0.028% magnesium chloride ($MgCl_2$); 0.28% calcium chloride ($CaCl_2$); 0.21% sodium carbonate ($NaHCO3$); and 0.18% glucose was prepared. This entailed gradual addition of the water soluble ingredients (i.e. Pluronic™, Starch, glycerol, salts and glucose, and DOPE) into the perfluorotripropylamine phase using sonication (Branson Series 7000 Ultrasonic Generator Model SH-1012-40-18S) over a period of 15 minutes (40 kHz, 8.5 amps).

What is claimed is:

1. A method of administering a bioactive agent to a mammal by parenterally administering to the mammal a composition comprising an emulsion which comprises:
   (a) the bioactive agent;
   (b) water;
   (c) a pharmaceutically acceptable oil having an HLB requirement of between about 8 and less than about 17.4; and,
   (d) a phospholipid surfactant comprising from about 5% to about 30% (w/w) of the emulsion and providing an HLB value equal to the HLB requirement of the oil,
   wherein dioleoyl phosphatidylethanolamine and a phosphatidylcholine having an HLB value of about 7.6 comprise 100% by weight of the phospholipid surfactant; wherein the weight percentage of dioleoyl phosphatidylethanolamine in the phospholipid surfactant and is from about 4.1% by weight of the phospholipid surfactant to less than 100% by weight of the surfactant; and,
   wherein the weight percentage of the phosphatidylcholine in the phospholipid surfactant is equal to 100% by weight of the surfactant minus the weight percentage of dioleoyl phosphatidylethanolamine in the surfactant and is from greater than about 0% by weight of the surfactant to at most about 95.9% by weight of the surfactant.

2. The method of claim 1, wherein the bioactive agent is an anti-inflammatory, antibacterial, antiviral, antiparasitic, antifungal, antineoplastic, neurotransmitting, hormonal, immunomodulating or perfluorocarbon agent.

3. The method of claim 2, wherein the agent is the hormone insulin.

4. The method of claim 1, wherein the parenteral administration comprises subcutaneous or intravenous administration.

5. The method of claim 1, wherein the emulsion is in cream or gel form.

6. The method of claim 1, wherein the pharmaceutically acceptable oil is castor, soy, safflower, cottonseed, peanut, palm, mineral or corn oil.

7. The method of claim 1, wherein the HLB requirement is from less than about 10 to about 17.4.

8. The method of claim 1, wherein the surfactant comprises about 20% (w/w) of the emulsion.

9. The method of claim 1, wherein the phosphatidylcholine is egg phosphatidylcholine.

10. The method of claim 1, wherein the surfactant comprises DOPE and the phosphatidylcholine in a respective weight ratio (%) of from about 35:65 to about 65:35.

11. The method of claim 1, wherein the phospholipid consists essentially of DOPE and egg phosphatidylcholine in a respective weight ratio (%) of about 65:35.

12. The method of claim 1, wherein the composition further comprises a pharmaceutically acceptable carrier.

* * * * *